US007378500B2

(12) United States Patent
Carney

(10) Patent No.: US 7,378,500 B2
(45) Date of Patent: *May 27, 2008

(54) USE OF THROMBIN-DERIVED PEPTIDES FOR THE THERAPY OF CHRONIC DERMAL ULCERS

(75) Inventor: Darrell H. Carney, Dickinson, TX (US)

(73) Assignee: Orthologic Corp., Tempe, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/397,310

(22) Filed: Apr. 4, 2006

(65) Prior Publication Data

US 2006/0241049 A1 Oct. 26, 2006

Related U.S. Application Data

(63) Continuation of application No. 10/766,752, filed on Jan. 27, 2004, now Pat. No. 7,049,294, which is a continuation of application No. PCT/US02/01151, filed on Jan. 16, 2002.

(60) Provisional application No. 60/308,198, filed on Jul. 27, 2001.

(51) Int. Cl.
*C07K 14/00* (2006.01)

(52) U.S. Cl. .................................... 530/350

(58) Field of Classification Search ............ None
See application file for complete search history.

(56) References Cited

U.S. PATENT DOCUMENTS 5,352,664 A * 10/1994 Carney et al. ............. 514/13
5,500,412 A    3/1996 Carney et al.

FOREIGN PATENT DOCUMENTS

WO   WO 88/03151      5/1988
WO   WO 96/40033     12/1996
WO   WO 01/49309 A2   7/2001

OTHER PUBLICATIONS

HGS, Backgounder, Internet Publication, Sep. 2000, pp. 1-3.*
Stiernberg, J., et al., "Acceleration of full-thickness wound healing in normal rats by the synthetic thrombin peptide, TP508," *Wound Repair and Regeneration*, 8(3):204-215 (2000).

Norfleet, A.M., et al., "Thrombin peptide, TP508, stimulates angiogenic responses in animal models of dermal wound healing, in chick chorioallantoic membranes, and in cultured human aortic and microvascular endothelial cells," *General Pharmacology*, 35:249-254 (2002).
Norfleet, A.M., et al., "Thrombin peptide TP508 accelerates closure of dermal excisions in animal tissue with surgically induced ischemia," *Wound Repair and Regeneration*, 8(6):517-529 (2000).
Pernia, S.D., et al., "A Synthetic Peptide Representing the Thrombin Receptor-Binding Domain Enhances Wound Closure In Vivo," *SAAS Bulletin: Biochem. & Biotech.*, 3:8-12 (1990).
Carney, Darrell H., "Postclotting Cellular Effects of Thrombin Mediated by Interaction with High-Affinity Thrombin Receptors," In *Thrombin Structure and Function*, Berliner, L.J. (ed.)(New York: Plenum Press), pp. 351-396 (1992).
Stiernberg, J., et al., "The Role of Thrombin and Thrombin Receptor Activating Peptide (TRAP-508) in Initiation of Tissue Repair," *Thrombosis and Haemostasis*, 70(1)158-162 (1993).
Carney, D.H., et al., "Enhancement of Incisional Wound Healing and Neovascularization in Normal Rats by Thrombin and Synthetic Thrombin Receptor-activating Peptides," *J. Clin. Invest.*, 89:1469-1477 (1992).
Carney, D.H., et al., "Role of High-Affinity Thrombin Receptors in Postclotting Cellular Effects of Thrombin," *Seminars in Thrombosis and Hemostasis*, 18(1):91-102 (1992).
Glenn, K.C., et al., "Synthetic Peptides Bind to High-Affinity Thrombin Receptors and Modulate Thrombin Mitogenesis," *Peptide Research*, 1(2):65-73 (1988).
Sower, L.E., et al., "Thrombin Peptide, TP508, Induces Differential Gene Expression in Fibroblasts through a Nonproteolytic Activation Pathway," *Experimental Cell Research*, 247:422-431 (1999).
Steed, D.L., et al., "Promotion and Acceleration of Diabetic Ulcer Healing by Arginine-Glycine-Aspartic Acid (RGD) Peptide Matrix," *Diabetes Care*, 18(1):39-46 (1995).
Press Release: Chrysalis BioTechnology to begin clinical trials, (Sep, 24, 1998).
Press Release: Chrysalis Announces Completion of Pilot Chrysalin® Clinical Trial for Diabetic Ulcers, (Aug. 21, 2001).
Hollenberg, Morley D., et al., "Synergistic Actions of a Thrombin-Derived Synthetic Peptide and a Thrombin Receptor-Activating Peptide in Stimulating Fibroblast Mitogenesis," *J. Cell Physiol.* 169:491-496 (1996).

* cited by examiner

*Primary Examiner*—Robert B. Mondesi
(74) *Attorney, Agent, or Firm*—Hamilton, Brook, Smith & Reynolds, P.C.

(57) ABSTRACT

Disclosed is a method of promoting healing of a chronic dermal skin ulcer, such as a diabetic ulcer, on a subject. The method comprises the step of contacting the chronic dermal skin ulcer with an effective amount of an agonist of the non-proteolytically activated thrombin receptor.

6 Claims, No Drawings

SEQUENCE LISTING

```
<160> NUMBER OF SEQ ID NOS: 9

<210> SEQ ID NO 1
<211> LENGTH: 23
<212> TYPE: PRT
<213> ORGANISM: Artificial Sequence
<220> FEATURE:
<223> OTHER INFORMATION: fragment of human thrombin

<400> SEQUENCE: 1

Ala Gly Tyr Lys Pro Asp Glu Gly Lys Arg Gly Asp Ala Cys Glu Gly
1               5                   10                  15

Asp Ser Gly Gly Pro Phe Val
            20

<210> SEQ ID NO 2
<211> LENGTH: 23
<212> TYPE: PRT
<213> ORGANISM: Artificial Sequence
<220> FEATURE:
<223> OTHER INFORMATION: thrombin peptide derivative
<220> FEATURE:
<223> OTHER INFORMATION: Alanine at position 1 is optionally N-acylated
<220> FEATURE:
<221> NAME/KEY: VARIANT
<222> LOCATION: 15
<223> OTHER INFORMATION: Valine at position 23 is optionally C-amidated
<220> FEATURE:
<221> NAME/KEY: VARIANT
<222> LOCATION: 22
<223> OTHER INFORMATION: Xaa = Glu or Gln
<220> FEATURE:
<223> OTHER INFORMATION: Xaa = Phe, Met, Leu, His or Val

<400> SEQUENCE: 2

Ala Gly Tyr Lys Pro Asp Glu Gly Lys Arg Gly Asp Ala Cys Xaa Gly
1               5                   10                  15

Asp Ser Gly Gly Pro Xaa Val
            20

<210> SEQ ID NO 3
<211> LENGTH: 33
<212> TYPE: PRT
<213> ORGANISM: Artificial Sequence
<220> FEATURE:
<223> OTHER INFORMATION: thrombin peptide derivative
<220> FEATURE:
<223> OTHER INFORMATION: Aspartic acid at position 1 is optionally
      N-Acylated
```

```
<220> FEATURE:
<223> OTHER INFORMATION: Phenylalanine at position 33 is optionally
      C-amidated

<400> SEQUENCE: 3

Asp Asn Met Phe Cys Ala Gly Tyr Lys Pro Asp Glu Gly Lys Arg Gly
 1               5                  10                  15

Asp Ala Cys Glu Gly Asp Ser Gly Gly Pro Phe Val Met Lys Ser Pro
            20                  25                  30

Phe

<210> SEQ ID NO 4
<211> LENGTH: 33
<212> TYPE: PRT
<213> ORGANISM: Artificial Sequence
<220> FEATURE:
<223> OTHER INFORMATION: thrombin peptide derivative
<220> FEATURE:
<223> OTHER INFORMATION: Aspartic acid at position 1 is optionally
      N-acylated.
<220> FEATURE:
<221> NAME/KEY: VARIANT
<222> LOCATION: 20
<223> OTHER INFORMATION: Aspartic acid at position 33 is optionally
      C-amidated
<220> FEATURE:
<221> NAME/KEY: VARIANT
<222> LOCATION: 27
<223> OTHER INFORMATION: Xaa = Glu or Gln
<220> FEATURE:
<223> OTHER INFORMATION: Xaa = Phe, Met, Leu, His or Val

<400> SEQUENCE: 4

Asp Asn Met Phe Cys Ala Gly Tyr Lys Pro Asp Glu Gly Lys Arg Gly
 1               5                  10                  15

Asp Ala Cys Xaa Gly Asp Ser Gly Gly Pro Xaa Val Met Lys Ser Pro
            20                  25                  30

Phe

<210> SEQ ID NO 5
<211> LENGTH: 23
<212> TYPE: PRT
<213> ORGANISM: Artificial Sequence
<220> FEATURE:
<223> OTHER INFORMATION: thrombin peptide derivative
<220> FEATURE:
<223> OTHER INFORMATION: Alanine at position 1 is optionally N-acylated
<220> FEATURE:
<223> OTHER INFORMATION: Valine at position 23 is optionally C-amidated

<400> SEQUENCE: 5

Ala Gly Tyr Lys Pro Asp Glu Gly Lys Arg Gly Asp Ala Cys Glu Gly
 1               5                  10                  15

Asp Ser Gly Gly Pro Phe Val
            20

<210> SEQ ID NO 6
<211> LENGTH: 23
<212> TYPE: PRT
<213> ORGANISM: Artificial Sequence
<220> FEATURE:
<223> OTHER INFORMATION: thrombin peptide derivative
<220> FEATURE:
<223> OTHER INFORMATION: Valine at position 23 is amidated with -NH2

<400> SEQUENCE: 6

Ala Gly Tyr Lys Pro Asp Glu Gly Lys Arg Gly Asp Ala Cys Glu Gly
```

```
                           -continued 1               5              10             15
Asp Ser Gly Gly Pro Phe Val
            20

<210> SEQ ID NO 7
<211> LENGTH: 4
<212> TYPE: PRT
<213> ORGANISM: Artificial Sequence
<220> FEATURE:
<223> OTHER INFORMATION: fragment of human thrombin

<400> SEQUENCE: 7

Arg Gly Asp Ala
 1

<210> SEQ ID NO 8
<211> LENGTH: 12
<212> TYPE: PRT
<213> ORGANISM: Artificial Sequence
<220> FEATURE:
<223> OTHER INFORMATION: fragment of human thrombin

<400> SEQUENCE: 8

Asp Ala Cys Glu Gly Asp Ser Gly Gly Pro Phe Val
 1               5                  10

<210> SEQ ID NO 9
<211> LENGTH: 12
<212> TYPE: PRT
<213> ORGANISM: Artificial Sequence
<220> FEATURE:
<223> OTHER INFORMATION: variant of human thrombin peptide fragment
<220> FEATURE:
<221> NAME/KEY: VARIANT
<222> LOCATION: 2
<223> OTHER INFORMATION: Xaa = Ala or Ser
<220> FEATURE:
<221> NAME/KEY: VARIANT
<222> LOCATION: 4
<223> OTHER INFORMATION: Xaa = Glu or Gln
<220> FEATURE:
<221> NAME/KEY: VARIANT
<222> LOCATION: 11
<223> OTHER INFORMATION: Xaa = Phe, Met Leu His or Val

<400> SEQUENCE: 9

Asp Xaa Cys Xaa Gly Asp Ser Gly Gly Pro Xaa Val
 1               5                  10
```

USE OF THROMBIN-DERIVED PEPTIDES FOR THE THERAPY OF CHRONIC DERMAL ULCERS

RELATED APPLICATIONS

This application is a continuation of U.S. patent application Ser. No. 10/766,752, filed Jan. 27, 2004, now U.S. Pat. No. 7,049,294, which is a continuation of International Application No. PCT/US02/01151, which designated the United States and was filed Jan. 16, 2002, published in English, which claims the benefit of U.S. Provisional Application Ser. No. 60/308,198, filed Jul. 27, 2001. The entire teachings of the above applications are incorporated herein by reference.

GOVERNMENT SUPPORT

The invention was supported, in whole or in part, by grant 1R01-GM47572 and R44-DK53580 from the National Institutes of Health. The Government has certain rights in the invention.

BACKGROUND OF THE INVENTION

Dermal skin ulcers are an example of wounds that are particularly difficult to treat because they resist healing and consequently often become chronic wounds. Examples of chronic dermal ulcers include those resulting from venous disease (venous stasis ulcers), excessive pressure (decubitus ulcers), arterial ulcers and diabetic ulcers.

Diabetic ulcers are particularly problematic. For example, one in seven individuals with diabetes develops dermal ulcers on their extremities, which are susceptible to infection. Treatment of diabetic ulcers is often prolonged, intensive and costly and treatment failures are common. Current approaches include debridement, frequent changes of wound dressing, specially fitted footwear, oral or intravenous antibiotics, complete bed rest, lengthy hospitalization and surgical revascularization. Ulcer-related complications can in some cases require amputation. Therefore, there is a need for treatments which accelerate the rate of the healing of chronic dermal skin ulcers in general, and of diabetic ulcers, in particular.

SUMMARY OF THE INVENTION

It has now been found that agonists of the non-proteolytically activated thrombin receptor are effective in accelerating the rate of healing of diabetic ulcers. For example, the thrombin peptide derivative TP508, administered topically twice a week at doses of 1.0 µg or 10.0 µg increased the rate at which diabetic ulcers healed and increased the percentage of patients who experienced 100% closure of the ulcer. Based on this discovery, methods of promoting or accelerating healing of chronic dermal ulcers are disclosed herein.

One embodiment of the present invention is a method of promoting healing of a chronic dermal skin ulcer on a subject. The method comprises the step of contacting the chronic dermal skin ulcer with an effective amount of an agonist of the non-proteolytically activated thrombin receptor.

The thrombin peptide derivatives used in the methods disclosed, herein are inexpensive to produce and are effective in accelerating the rate at which chronic dermal skin ulcers heal and in increasing the likelihood of complete closure of the ulcer. They also cause few, if any, side effects.

DETAILED DESCRIPTION OF THE INVENTION

Dermal skin ulcers refer to lesions on the skin caused by superficial loss of tissue that fail to heal normally due to defects in healing processes, vascular insufficiency or pressure. Dermal skin ulcers which can be treated by the method of the present invention include decubitus ulcers, diabetic ulcers, venous stasis ulcers and arterial ulcers. Decubitus wounds refer to chronic ulcers that result from pressure applied to areas of the skin for extended periods of time. Wounds of this type are often called bedsores or pressure sores. Venous stasis ulcers result from the stagnation of blood or other fluids from defective veins. Arterial ulcers refer to necrotic skin in the area around arteries having poor blood flow.

Applicants have discovered that compounds which stimulate or activate the non-proteolytically activated thrombin receptor (hereinafter "NPAR") promote or stimulate healing of chronic dermal skin ulcers. Compounds which stimulate NPAR are said to be NPAR agonists. NPAR is a high-affinity thrombin receptor present on the surface of most cells. This NPAR component is largely responsible for high-affinity binding of thrombin, proteolytically inactivated thrombin, and thrombin derived peptides to cells. NPAR appears to mediate a number of cellular signals that are initiated by thrombin independent of its proteolytic activity. An example of one such signal is the upregulation of annexin V and other molecules identified by subtractive hybridization (see Sower, et. al., *Experimental Cell Research* 247:422 (1999)). NPAR is therefore characterized by its high affinity interaction with thrombin at cell surfaces and its activation by proteolytically inactive derivatives of thrombin and thrombin derived peptide agonists as described below. NPAR activation can be assayed based on the ability of molecules to stimulate cell proliferation when added to fibroblasts in the presence of submitogenic concentrations of thrombin or molecules that activate protein kinase C as disclosed in U.S. Pat. Nos. 5,352,664 and 5,500,412. The entire teachings of these patents are incorporated herein by reference. NPAR agonists can be identified by this activation or by their ability to compete with $^{125}$I-thrombin binding to cells.

NPAR agonists include thrombin derivatives described in U.S. Pat. Nos. 5,352,664 and 5,500,412. For example, a thrombin peptide derivative can comprise a thrombin receptor binding domain having the L-amino acid sequence Arg-Gly-Asp-Ala (SEQ ID NO: 7), and a serine esterase conserved sequence. In one embodiment, a peptide derivative of thrombin comprises a serine esterase conserved sequence, Asp-Ala-Cys-Glu-Gly-Asp-Ser-Gly-Gly-Pro-Phe-Val (SEQ ID NO: 8). One example of an NPAR agonist is a thrombin peptide derivative, i.e., a polypeptide with less than about fifty amino acids, preferably less than about thirty-three amino acids and having sufficient homology to the fragment of human thrombin corresponding to prothrombin amino acids 508-530 (Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val: SEQ ID NO.: 1) that the polypeptide activates NPAR. The thrombin peptide derivatives described herein preferably have between about 14 and 23 amino acids, more preferably between about 19 and 23 amino acids. Optionally, the thrombin peptide derivatives described herein can be amidated at the C-terminus and/or acylated at the N-terminus. In one embodiment, the thrombin peptide derivative being administered to the chronic skin ulcer has the following amino acid sequence: R1-Ala-Gly-Tyr-Lys-Pro-Asp-Glu-Gly-Lys-Arg-Gly-Asp-Ala-Cys-Glu-Gly-Asp-Ser-Gly- Gly-Pro-Phe-Val-R2: SEQ ID NO.: 5. R1 is —H or R3-C(O)—; R2 is —OH or —NR4R5; R3 is —H or C1-C6 alkyl group (preferably —CH$_3$); and R4 and R5 are independently —H, C1-C6 alkyl group or, taken together with the nitrogen atom to which they are bonded, are a non-aromatic heterocyclic group such a piperidinyl, morpholinyl, thiomorphinyl or pyrollidinyl (preferably R4 and R5 are both —H). Preferably R1 is —H and R2 is —NH$_2$; or R1 is —H and R2 is —OH. Alternatively, the thrombin peptide derivative being administered to the chronic skin ulcer has the amino acid sequence of SEQ ID NO.: 3: R1-Asp-Asn-Met-Phe-Cys-Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-Met-Lys-Ser-Pro-Phe-R2 are as described above. It is understood, however, that zero, one, two or three amino acids at positions 1-9 and 14-23 in the thrombin peptide derivative can differ from the corresponding amino acid in SEQ ID NO.: 5. It is also understood that zero, one, two or three amino acids at positions 1-14 and 19-33 in the thrombin peptide derivative can differ from the corresponding amino acid in SEQ ID NO.: 3. Preferably, the amino acids in the thrombin peptide derivative which differ from the corresponding amino acid in SEQ ID NO.: 3 or SEQ ID NO.: 5 are conservative substitutions, and are more preferably highly conservative substitutions. Alternatively, an N-terminal truncated fragment of the thrombin peptide derivatives having at least fourteen amino acids or a C-terminal truncated fragment of the thrombin peptide derivative having at least eighteen amino acids can be contacted with the chronic skin ulcer.

A thrombin receptor binding domain is defined as a polypeptide sequence which directly binds to the thrombin receptor and/or competitively inhibits binding between high-affinity thrombin receptors and alpha-thrombin.

A domain having a serine esterase conserved sequence comprises a polypeptide sequence containing at least 4-12 of the N-terminal amino acids of the dodecapeptide previously shown to be highly conserved among serine proteases (Asp-X$_1$-Cys-X$_2$-Gly-Asp-Ser-Gly-Gly-Pro-X$_3$-Val; SEQ ID NO: 9); wherein X$_1$ is either Ala or Ser; X$_2$ is either Glu or Gln; and X$_3$ is either Phe, Met, Leu, His, or Val).

A "C-terminal truncated fragment" refers to a fragment remaining after removing an amino acid or block of amino acids from the C-terminus. An "N-terminal truncated fragment" refers to a fragment remaining after removing an amino acid or block of amino acids from the N-terminus. It is to be understood that the terms "C-terminal truncated fragment" and "N-terminal truncated fragment" encompass acylation at the N-terminus and/or amidation at the C-terminus, as described above.

A peptide is acylated at the N-terminus when the amine —NH$_2$ at the N-terminus is derivatized as an acyl group R3-C(O)—NH—, wherein R3 is as described above. Thus, when R1 is R3-C(O)—, the N-terminus is an acyl group; and when R1 is —H, the N-terminus is an unsubstituted amine.

A peptide is amidated at the C-terminus when the carboxylic acid —COOH at the C-terminus is derivatized as an amide —CONR4R5, wherein R4 and R5 are as described above. Thus, when R2 is —OH, the C-terminus is a carboxylic acid; and when R2 is —NR4R5, the C-terminus is amidated.

A preferred thrombin peptide derivative for use in the disclosed method has the amino acid sequence of SEQ ID NO.: 2: R1-Ala-Gly-Try-Lys-Pro-Asp-Glu-Gly-Lys-Arg-Gly-Asp-Ala-Cys-X$_1$-Gly-Asp-Ser-Gly-Gly-Pro-Val-R2. R1 and R2 are as described above. Another preferred thrombin peptide derivative for use in the disclosed method has the amino acid sequence of SEQ ID NO.: 4: R1-Asp-Asn-Met-Phe-Cys-Ala-Gly-Try-Lys-Pro-Asp-Glu-Gly-Lys-Arg-Gly-Asp-Ala-Cys-X$_1$-Gly-Asp-Ser-Gly-Gly-Pro-X$_2$-Val-Met-Lys-Ser-Pro-Phe-R2. X$_1$ is Glu or Gln; X$_2$ is Phe, Met, Leu, His or Val; and R1 and R2 are as described above. Alternatively, N-terminal truncated fragments of these preferred thrombin peptide derivatives, the N-terminal truncated fragments having at least fourteen amino acids or C-terminal truncated fragments of these preferred thrombin peptide derivative, the C-terminal truncated fragments having at least eighteen amino acids, can also be used in the disclosed method.

TP508 is an example of a thrombin peptide derivative and has the amino acid sequence of SEQ ID NO.: 5, wherein R1 is —H and R2 is —NH$_2$ (SEQ ID NO.: 6). Another example of a thrombin peptide derivative has the amino acid sequence of SEQ ID NO.: 5, wherein R1 is —H and R2 is —OH ("deamide TP508"). Other examples of thrombin peptide derivatives which can be used in the disclosed method include N-terminal truncated fragments of TP508 (or deamide TP508), the N-terminal truncated fragments having at least fourteen amino acids or C-terminal truncated fragments of TP508 (or deamide TP508), the C-terminal truncated fragments having at least eighteen amino acids.

A "conservative substitution" is the replacement of an amino acid with another amino acid that has the same net electronic charge and approximately the same size and shape. Amino acids with aliphatic or substituted aliphatic amino acid side chains have approximately the same size when the total number carbon and heteroatoms in their side chains differs by no more than about four. They have approximately the same shape when the number of branches in the their side chains differs by no more than one. Amino acids with phenyl or substituted phenyl groups in their side chains are considered to have about the same size and shape. Listed below are five groups of amino acids. Replacing an amino acid in a polypeptide with another amino acid from the same group results in a conservative substitution:

Group I: glycine, alanine, valine, leucine, isoleucine, serine, threonine, cysteine, and non-naturally occurring amino acids with C1-C4 aliphatic or C1-C4 hydroxyl substituted aliphatic side chains (straight chained or mono-branched).

Group II: glutamic acid, aspartic acid and non-naturally occurring amino acids with carboxylic acid substituted C1-C4 aliphatic side chains (unbranched or one branch point).

Group III: lysine, ornithine, arginine and non-naturally occurring amino acids with amine or guanidino substituted C1-C4 aliphatic side chains (unbranched or one branch point).

Group IV: glutamine, asparagine and non-naturally occurring amino acids with amide substituted C1-C4 aliphatic side chains (unbranched or one branch point).

Group V: phenylalanine, phenylglycine, tyrosine and tryptophan.

A "highly conservative substitution" is the replacement of an amino acid with another amino acid that has the same functional group in the side chain and nearly the same size and shape. Amino acids with aliphatic or substituted aliphatic amino acid side chains have nearly the same size when the total number carbon and heteroatoms in their side chains differs by no more than two. They have nearly the same shape when they have the same number of branches in the their side chains. Example of highly conservative substitutions include valine for leucine, threonine for serine, aspartic acid for glutamic acid and phenylglycine for phenylalanine. Examples of substitutions which are not highly conservative include alanine for valine, alanine for serine and aspartic acid for serine.

A "subject" is preferably a human, but can also be an animal in need of treatment, e.g., companion animals (e.g., dogs, cats, and the like), farm animals (e.g., cows, pigs, horses and the like) and laboratory animals (e.g., rats, mice, guinea pigs and the like).

The composition used in the present invention to promote healing of chronic dermal ulcers can additionally comprise a pharmaceutical carrier suitable for local topical administration in which the thrombin peptide derivative or NPAR agonist is dissolved or suspended. Examples of pharmaceutically acceptable carriers include, for example, saline, aerosols, commercially available inert gels, or liquids supplemented with albumin, methyl cellulose or a collagen matrix. Typical of such formulations are ointments, creams and gels. Ointments are typically prepared using an oleaginous base, e.g., containing fixed oils or hydrocarbons, such as white petrolatum or mineral oil, or an absorbent base, e.g., consisting of an absorbent anhydrous substance or substances, for example anhydrous lanolin. Following formation of the base, the active ingredients are added in the desired concentration. Creams generally comprise an oil phase (internal phase) containing typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia colloidal clays, beegum, and the like. Upon formation of the emulsion, the active ingredients are added in the desired concentration. Gels are comprised of a base selected from an oleaginous base, water, or an emulsion-suspension base, as previously described. To the base is added a gelling agent which forms a matrix in the base, increasing its viscosity to a semisolid consistency. Examples of gelling agents are hydroxypropyl cellulose, acrylic acid polymers, and the like. The active ingredients are added to the formulation at the desired concentration at a point preceding addition of the gelling agent or can be mixed after the gelation process.

The present invention is directed to promoting healing of chronic dermal skin ulcers. A method of treatment "promotes healing" when that the chronic dermal skin ulcer heals more rapidly with the treatment than in the absence of treatment. Alternatively, a method of treatment "promoting healing" when there is a greater likelihood that the chronic dermal skin ulcer will completely heal than in the absence of the treatment.

An "effective amount" is the quantity of NPAR agonist or thrombin peptide derivative which results in greater wound healing and increased growth and proliferation of endothelial cells, keratinocytes and fibroblasts than in the absence of the NPAR agonist or thrombin peptide derivative. Alternatively, an "effective amount" is the quantity of NPAR agonist or thrombin peptide derivative which results in a greater likelihood that the chronic dermal ulcer will completely heal than in the absence of the NPAR agonist or thrombin peptide derivative. The agonist is administered for a sufficient period of time to achieve the desired therapeutic effect. The amount administered will depend on the amount of dermal growth that is desired, the health, size, weight, age and sex of the subject, the nature of the chronic dermal skin ulcer (e.g., the type of dermal skin ulcer severity). Typically, between about 0.1 µg per day and about 1 mg per day of NPAR agonist or thrombin peptide derivative (preferably between about 1 µg per day and about 100 µg per day) is administered by direct application to the chronic dermal skin ulcer. Generally, enough pharmaceutical carrier or inert solvent is used to cover the wound.

In certain instances where chronic dermal skin ulcers are being treated, it may be advantageous to co-administer one or more additional pharmacologically active agents to the chronic dermal skin ulcer along with a thrombin peptide derivative or NPAR agonist. For example, infection is a threat with any chronic dermal skin ulcer. One aspect of the present invention is to co-administer to the chronic dermal skin ulcer an antimicrobial, a disinfectant or an antibiotic. Managing pain and inflammation are also important aspects of treating chronic dermal skin ulcers. NPAR agonists and thrombin peptide derivatives can also be co-administered to a chronic dermal skin ulcer along with a pain-relieving agent such as an analgesic or an anti-inflammatory agent.

Thrombin peptide derivatives can be synthesized by solid phase peptide synthesis (e.g., BOC or FMOC) method, by solution phase synthesis, or by other suitable techniques including combinations of the foregoing methods. The BOC and FMOC methods, which are established and widely used, are described in Merrifield, *J. Am. Chem. Soc.* 88:2149 (1963); Meienhofer, *Hormonal Proteins and Peptides*, C. H. Li, Ed., Academic Press, 1983, pp. 48-267; and Barany and Merrifield, in *The Peptides*, E. Gross and J. Meienhofer, Eds., Academic Press, New York, 1980, pp. 3-285. Methods of solid phase peptide synthesis are described in Merrifield, R. B., *Science*, 232: 341 (1986); Carpino, L. A. and Han, G. Y., *J. Org. Chem.*, 37: 3404 (1972); and Gauspohl, H. et al., *Synthesis*, 5: 315 (1992)). The teachings of these six articles are incorporated herein by reference in their entirety.

The invention is illustrated by the following examples which are not intended to be limiting in any way.

EXEMPLIFICATION

Methodology—Study Design

This study was a multi-center, randomized, double blind, three-arm Phase IIa pilot study evaluating synthetic thrombin peptide TP508 for accelerating the healing of chronic diabetic ulcers. Patients were randomized to one of three topical treatment groups: 1 microgram of TP508 in saline applied twice weekly, 10 micrograms of TP508 in saline applied twice weekly, or saline placebo applied twice weekly. All patients received a regimen of standard diabetic ulcer care consisting of initial sharp debridement, wound cleansing, wound dressing, and wound pressure offloading. Wounds were evaluated twice a week for up to 20 weeks or until wound closure, whichever was earlier. Patients were removed from the study if they developed a clinical infection or if the wound condition significantly deteriorated. At each wound evaluation (twice weekly), the wound perimeter was traced for determination of wound area, and the wound was photographed with a digital camera. Blood chemistry and hematology tests were performed at patient enrollment, and at weeks 5, 10, 15, and 20. A radiographic assessment was conducted every 5 weeks to study effects on underlying bone composition.

Inclusion/Exclusion Criteria

Males and females ranging in age from 30 to 65 years of age were allowed to participate in the study. Females of childbearing potential had to use an acceptable method of birth control and were urine tested for pregnancy prior to entering the study. To be enrolled in the study, a patient's diabetic pathology had to be clinically documented via blood glucose and HgbAlC, but other than the diabetic condition, the patient had to be in reasonably good health. The ulcer to be treated (study ulcer) had to be located below the kneecap, Wagner Grade 1 (wound had to pass through the epidermis and into the dermis), Grade 2, or mild Grade 3 to the periosteum (without bone or tendon involvement). The study ulcer had to be between 1.0 cm diameter (0.9cm$^2$ area) and 7.0 cm diameter (about 38.5 cm$^2$ area). The study ulcer must also have been present for a minimum of eight (8) weeks and a maximum of two (2) years without healing during that time. The patients' wound oxygen tension (TcPO2) measurement at baseline had to be greater than or equal to 20 mmHg as measured by heated oxygen sensors. In addition, patients were required to be capable of comprehending and following study instructions, complying with the treatment regimen and any prescribed wound pressure offloading, and providing informed consent.

Number of Patients (Planned and Analyzed)

The study was planned for a total enrollment of 60 patients, with 20 patients per treatment arm. A total of 60 patients were enrolled and treated in the study. Of these 60 patients, 12 patients discontinued from the study prematurely. Four patients discontinued due to infected wounds, two discontinued due to osteomyelitis, one patient discontinued because of amputation, one patient discontinued because of myocardial infarction, two patients withdrew from the study for non-medical reasons, one patient due to wound worsening, and one patient took a disallowed medication. None of the causes of study discontinuation were related to drug use.

Efficacy (i)

The primary efficacy endpoint was the proportion of patients that achieve full wound closure. Full wound closure was defined as 100% epithelialization, with no drainage and no infection, as determined by visual inspection by the clinician. The difference in proportions between the treatment groups was compared. Secondary endpoints included the time to 100% closure of the study wound, the time to 80% and 50% wound closure, and the amount of wound closure (as a percentage change from baseline wound size) at 3, 5, 10, 15, and 20 weeks.

Efficacy (ii)

Three different patient analysis groups were defined to better study the efficacy endpoints. The Intent-To-Treat (ITT) group included all 60 patients receiving study drug and was primarily used for safety evaluation. The Per-Protocol group included 40 patients that met a predefined set of criteria meant to assure the highest compliance with the protocol. The Efficacy Group included 46 patients which met standards that were chosen prior to unblinding to be most relevant to allow an accurate evaluation of wound healing. Primary and secondary endpoint results are described for each patient group. Similar positive dose response trends for treatment effect in the primary endpoint were seen in all treatment groups, with the effect most pronounced in the Per-Protocol Group.

Primary Endpoint

The primary efficacy endpoint was the percentage of patients achieving full wound closure within twenty weeks. The table below summarizes the results of the primary efficacy endpoint of closure for the three analysis populations:

|  | 100% Closure Rate | | |
| --- | --- | --- | --- |
|  | Saline (%) | 1.0 µg (%) | 10.0 µg (%) |
| PP | 5/15 (33) | 5/11 (45) | 8/14 (57) |
| ITT | 10/21 (48) | 11/21 (52) | 11/18 (61) |
| EF | 6/16 (38) | 8/15 (53) | 9/16 (60) |

PP—Per Protocol Population
ITT—Intent-To-Treat Population
EF—Efficacy Population These results show a dose response relationship for 100% closure in all populations examined, with 1.0 µg treatments resulting in four to fifteen percent more closure than saline placebo controls, and 10 µg treatments resulting in thirteen to twenty four percent more closure than saline placebo controls. Specifically, in the per protocol treatment group (PP), five of fifteen or 33% healed in the saline placebo group, five of eleven or 45% healed in the 1 µg treatment group, and eight of fourteen or 57% healed in the 10 µg group. In the efficacy (EF) group selected to include wounds slightly smaller and slightly larger than those in the stricter per protocol group, this trend was again seen with 38% healing in the placebo group, 53% healing in the 1 µg group, and 60% healing in the 10 µg group. The difference was again noted in the intent to treat (ITT) population, although the percentage that healed in the saline placebo group was larger (48%) because this group included several small and superficial wounds that healed, but did not meet protocol to be defined as chronic diabetic wounds for the study.

These results compare favorably to clinical trials for Regranex®, where data compiled from four controlled randomized clinical trials show that 83 of 254 or 33% of the vehicle placebo wounds healed by 20 weeks and 122 of 285 or 43% of the Regranex®-treated wounds healed by 20 weeks (see FOI, FDA Clinical Review of BLA-96-1408, OMJ Pharmaceuticals, Dec. 9, 1997, page 55, and http://www.fda.gov/cber/products.becamj121697.htm, updated Mar. 5, 2001 and accessed Jul. 25, 2001; the entire teachings of these publications are incorporated herein by reference).

Secondary Endpoints

Secondary endpoints include the time to 100% closure, time to 80% closure, time to 50% closure, and the amount of wound closure as a percentage change from the baseline wound size at 3, 5, 10, 15, and 20 weeks. Kaplan-Meier survival analysis techniques were utilized to examine the time-to-event endpoints.

In the per-protocol population, the median time to 100% closure was 87 days for the 10 µg treatment group, versus 122 days for the 1 µg treatment group. The median time to 100% closure was not reached by 140 days in the saline control group. Thus, the healing time in this per protocol group appears to be shortened in the 10 µg treatment group by at least 53 days relative to placebo controls. The Kaplan-Meier analysis for time to 100% closure in the per protocol population predicts that by 14 weeks there would be a 30% probability of a placebo control wound closing, about 40% probability of the 1 µg treated wounds closing, and greater than 60% probability of wounds treated with 10 µg closing.

A similar dose effect was seen in the time to 80% wound closure with the median time to 80% closure of 32 days for the 10 µg treatment group, versus 47 days for the 1 µg treatment group and 57 days for the saline control group.

There was not an obvious dose effect in the time to 50% wound closure with the median time to 50% closure being 21 days in the 10 μg group versus 32 days in the 1 μg treatment group and 28 days for the saline control group.

In the efficacy population, the median time to 100% wound closure was 87 days for the 10 μg treatment group versus 116 days for the 1 μg group. The median time to 100% closure was not reached in the saline control group. For time to 80% wound closure, the median time was 46 days in the 10 μg dose group versus 49 days in the 1 μg dose group and 39 days in the saline control group. For the time to 50% closure, the median time was 21 days in the 10 μg treatment group versus 29 days and 28 days for the 1 μg and saline control groups, respectively.

In the intent-to-treat population, the median time to 100% wound closure was 87 days for the 10 μg treatment group versus 105 days for the 1 μg group and 102 days for the saline control group. For time to 80% wound closure, the median time was 31 days in the 10 μg dose group versus 49 days in the 1 μg dose group and 29 days in the saline control group. For the time to 50% closure, the median time was 17 days in the 10 μg treatment group versus 29 days and 17.5 days for the 1 μg and saline control groups, respectively.

These results show an increased percentage of ulcer closure for patients treated with TP508 and indicate median healing times that reflect a faster rate of healing.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating a chronic ulcer below the kneecap in a diabetic subject in need of treatment, said method comprising administering to the ulcer an effective amount of the polypeptide Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-NH$_2$ (SEQ ID NO:6), wherein the polypeptide is administered to the ulcer alone or in combination with an antimicrobial, a disinfectant, an antibiotic, an analgesic or an anti-inflammatory agent.

2. A method of treating a decubitus ulcer in a subject in need of treatment, said method comprising administering to the ulcer an effective amount of the polypeptide Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-NH$_2$ (SEQ ID NO:6), wherein the polypeptide is administered to the ulcer alone or in combination with an antimicrobial, a disinfectant, an antibiotic, an analgesic or an anti-inflammatory agent.

3. A method of treating a chronic ulcer below the kneecap in a diabetic subject in need of treatment, said method comprising administering to the ulcer an effective amount of the polypeptide Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-NH$_2$ (SEQ ID NO:6), wherein the polypeptide is administered to the ulcer alone or in combination with an antimicrobial, a disinfectant, an antibiotic, an analgesic or an anti-inflammatory agent, the method further comprising debriding the ulcer, cleansing the ulcer, dressing the ulcer, and offloading pressure from the ulcer.

4. A method of treating a decubitus ulcer in a subject in need of treatment, said method comprising administering to the ulcer an effective amount of the polypeptide Ala-Gly-Tyr-Lys-Pro-Asp-Glu-Gly-Lys-Arg-Gly-Asp-Ala-Cys-Glu- Gly-Asp-Ser-Gly-Gly-Pro-Phe-Val-NH₂ (SEQ ID NO:6), wherein the polypeptide is administered to the ulcer alone or in combination with an antimicrobial, a disinfectant, an antibiotic, an analgesic or an anti-inflammatory agent, the method further comprising debriding the ulcer, cleansing the ulcer, dressing the ulcer, and offloading pressure from the ulcer.

5. A method of treating a chronic ulcer below the kneecap in a diabetic subject in need of treatment, said method comprising administering to the ulcer an effective amount of the polypeptide Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-NH₂ (SEQ ID NO:6), wherein the polypeptide is administered to the ulcer for a period of at least 32 days, alone or in combination with an antimicrobial, a disinfectant, an antibiotic, an analgesic or an anti-inflammatory agent.

6. Method of treating a decubitus ulcer in a subject in need of treatment, said method comprising administering to the ulcer an effective amount of the polypeptide Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-NH₂ (SEQ ID NO:6), wherein the polypeptide is administered to the ulcer for a period of at least 32 days, alone or in combination with an antimicrobial, a disinfectant, an antibiotic, an analgesic or an anti-inflammatory agent.

* * * * *